US006408704B1

(12) United States Patent
Willeke (10) Patent No.: US 6,408,704 B1
(45) Date of Patent: *Jun. 25, 2002

(54) AERODYNAMIC PARTICLE SIZE ANALYSIS METHOD AND APPARATUS

(76) Inventor: Klaus Willeke, 147 Ritchie Ave., Cincinnati, OH (US) 45215-2062

(*) Notice: Subject to any disclaimer, the term of this patent is extended or adjusted under 35 U.S.C. 154(b) by 0 days.

This patent is subject to a terminal disclaimer.

(21) Appl. No.: 09/555,007
(22) PCT Filed: Feb. 1, 1999
(86) PCT No.: PCT/US99/02138
§ 371 (c)(1), (2), (4) Date: Aug. 14, 2000
(87) PCT Pub. No.: WO99/41588
PCT Pub. Date: Aug. 19, 1999

(51) Int. Cl.[7] ..................... G01N 15/00

(52) U.S. Cl. ..................... 73/865.5

(58) Field of Search ..................... 73/863.21, 863.22, 73/28.04–28.06, 865.5; 356/438, 439, 335, 336

(56) References Cited

U.S. PATENT DOCUMENTS

| | | | | |
|---|---|---|---|---|
| 3,790,760 A | | 2/1974 | Stiller | |
| 4,056,969 A | * | 11/1977 | Barringer | 73/28.05 |
| 4,152,923 A | | 5/1979 | Courbon | |
| 4,633,714 A | | 1/1987 | Mazumder et al. | |
| 4,895,034 A | | 1/1990 | Poole | |
| 5,090,233 A | * | 2/1992 | Kogure et al. | 73/863.22 |
| 5,296,910 A | | 3/1994 | Cole | |
| 5,561,515 A | | 10/1996 | Hairston et al. | |
| 5,679,907 A | | 10/1997 | Ruck | |
| 5,701,012 A | | 12/1997 | Ho | |
| 5,796,480 A | | 8/1998 | Igushi | |

* cited by examiner

*Primary Examiner*—Robert Raevis
(74) *Attorney, Agent, or Firm*—Wood, Herron & Evans, L.L.P.

(57) ABSTRACT

A method and apparatus are provided for measuring the aerodynamic particle size distribution of airborne particles by drawing the particles through a device **10*a* which continuously or intermittently changes the aerodynamic cut of the particles entering an aerosol sensor. Sensing is performed by optical sensors 16 such as aerosol photometry or optical single particle size spectrometry or by other sensors that measure particle concentration remaining in the aerosol flowing from the cut device. Preferably, the cut device includes a rotational element 22 that centrifugally removes particles of larger aerodynamic size than that determined by a cut setting, which can be varied by varying the rotational speed of the cut element. Preferably also, the rotary element does not alone determine the flow rate of the aerosol through the cut device, but a separate pump 40** or flow restriction controls the time the aerosol remains in the cut device and maintains the flow rate through the device at a preferably constant level.

38 Claims, 7 Drawing Sheets

AERODYNAMIC PARTICLE SIZE ANALYSIS METHOD AND APPARATUS

This is a U.S. national phase of PCT Application No. PCT/US99/02138, filed Feb. 1, 1999, which claims priority to U.S. patent application Ser. No. 09/024,341, filed Feb. 17,1998, now U.S. Pat. No. 5,949,001, and U.S. patent application Ser. No. 09/224,784, filed Jan. 4, 1999, now abandoned, which is a Continuation-in-Part of said U.S. patent application Ser. No. 09/024,341, filed Feb. 17, 1998.

FIELD OF THE INVENTION

The present invention relates to methods and devices for measuring airborne particles. In particular, the present invention relates to a method and apparatus for determining the concentrations of airborne particles in an aerosol as a function of aerodynamic particle size.

BACKGROUND OF THE INVENTION

The control of industrial and other environments increasingly requires ongoing knowledge of the quantities of airborne particles in the atmosphere. Dust and other non-gaseous particles are found suspended in air or other gaseous media. Such particles suspensions are referred to herein as aerosols. The effects of airborne particles as well as the control of airborne particles are dependent on the ways that the different particles move.

The motion in air of airborne particles and the deposition of such particles onto surfaces depends primarily on physical particle size. However, density, shape, surface properties and other characteristics of the particles also influence their airborne behavior. Usually these characteristics as well as all characteristics that affect particle motion and deposition are combined with the physical particle size into a property referred to as "aerodynamic particle diameter" or "aerodynamic particle size". A common method for determining the size distribution of particles in a volume of air, or the "aerosol size distribution" of the particles, is to collect the airborne or "aerosol" particles on a filter and to subsequently size them under an optical or electron microscope. However, this method only yields the physical size, not the aerodynamic particle size. To determine how these particles behave in air, in addition to determining the physical particle size by this method, it would be necessary to determine the other characteristics of the particles that will affect their airborne behavior. This technique is time consuming. Therefore, methods of dynamically measuring the sizes of particles dynamically, while suspended in air, have been preferred.

A common method for dynamically measuring the concentration and size distribution of particles in the airborne state uses techniques such as optical single particle size spectrometry. In this method, one particle at a time is passed through an illuminated view volume, and the magnitude of light scattered by each particle is recorded. An optical single particle counter when used with this method is usually calibrated with spherical, monodisperse test particles of known particle density and optical characteristics, such as polystyrene latex (PSL) spheres. However, most airborne particles have their own light scattering and absorption characteristics, so that the "optical particle diameter" measured by single particle size spectrometry generally does not correspond to the "aerodynamic particle diameter".

When using the optical single particle counting method, the device embodying this method can be dynamically calibrated to measure aerodynamic particle size by placing an impaction stage at its inlet. An impaction stage eliminates, from the aerosol, particles having an aerodynamic size above an aerodynamic threshold or "aerodynamic cut". The aerodynamic cut of an impaction stage can be determined by theory or experiment. Through this type of calibration, each optical particle size of the optical single particle counter can be related to its equivalent aerodynamic particle size. To operate an optical single particle counter in the field, the impaction stage is removed from the inlet. When an optical single particle counter is calibrated over a wide particle size range, several impaction stages with different aerodynamic cut sizes are successively attached to the optical single particle counter's inlet. This calibration is done for each aerosol of a different anticipated airborne particle composition. Such a calibration process is very time consuming.

A simpler dynamic optical particle sensing method is "aerosol photometry". In an aerosol photometer, the optical view volume is larger than in an optical single particle counter, thus accommodating a cloud of particles. However, the output from such a device depends not only on the optical characteristics of the particles, but also on the size distribution of all of the particles in the view volume. The light scattered by each particle depends on its refractive index and size.

Another dynamic, but more complex and expensive method for determining the aerodynamic particle size distribution in situ is by accelerating the aerosol particles in a nozzle and then measuring the "time of flight" of each particle between two points. In a nozzle or other acceleration field, aerodynamic drag accelerates large particles to a lesser extent than small particles. Thus, in an acceleration field, the time of flight between two points is longer for large particles than for small particles. The difference is caused by the difference in aerodynamic drag. Thus, this method determines the particle size distribution through a number of different techniques and geometric arrangements, as illustrated, for example, in U.S. Pat. Nos. 4,633,714; 5,296, 910; 5,561,515; 5,679,907; and 5,701,012.

Based on the above, there remains a need for a more efficient and more easily used method and apparatus for measuring the concentrations of airborne particles, and particularly for determining the aerodynamic particle size distribution in an aerosol.

SUMMARY OF THE INVENTION

An objective of the present invention is to determine the concentrations of airborne particles in an aerosol as a function of aerodynamic particle size. A further objective of the present invention is to provide a method and apparatus by which airborne particle concentration in an aerosol can be simply, economically and rapidly determined.

A particular objective of the present invention is to provide a method and apparatus for dynamically measuring concentrations of airborne particles in an aerosol as a function of their aerodynamic particle sizes or diameters.

According to the principles of the present invention, an aerosol, or air that contains airborne particles, is passed through an aerodynamic cut device which performs an aerodynamic cut of the particles entering an aerosol particle sensor. The airborne particles in the aerosol can be any inert or viable airborne particles, examples of which include dust, fume, smoke, fog, mist, bacteria, pollen, fungal spores, fragments of biological or non-biological material and other non-gaseous particles, or combinations thereof. Preferably, the aerodynamic cut is achieved by a rotating element in the aerodynamic cut device that centrifugally removes from the aerosol particles above or below a specific aerodynamic cut size.

In accordance with the preferred embodiment of the invention, the aerodynamic cut is achieved by a rotating element in the aerodynamic cut device which centrifugally removes particles above a predetermined or selected aerodynamic particle size from the aerosol, preferably to a collecting surface within the aerodynamic cut device. The rotating element may include one or more disc or propeller blades mounted on a rotating shaft, or an impeller with radial, forward-curved or backward-curved blades or other structure that accelerates particles outwardly from the axis of the rotating element. The collecting surface may be an inner wall of the housing containing the rotating element or a rotating enclosure or may be an enclosure that contains the rotating blade or other such structure and which rotates with such structure about its axis of rotation.

In certain preferred embodiments of the present invention, the aerodynamic cut is continuously or intermittently varied by variably controlling the configuration or motion of the rotating element of the cut device so as to change the distribution of particles in the aerosol entering an inlet of an aerosol particle sensor. Preferably, the variation of the rotating element is achieved by operating the element at a sequence of rotational speeds, preferably a sequence in which the rotational speeds are varied from zero through a plurality of discrete increasingly higher rotational speeds. Variation may also include sequentially or continuously adjusting the positions of the blades or other components of the rotating element so as to differently affect the centrifugal motion of the particles in the aerodynamic cut device.

As a result of the variations, a series of aerosols containing particles of sizes larger than the aerodynamic cuts determined by the set rotational speeds or other cut settings of the cut device are measured. The series of measurements are taken with an aerosol sensor of the particles remaining in the aerosol after each cut. Each of the measurements may, in this way, include a single analog measurement of the total particle content or concentration remaining in the aerosol after the cut. Preferably, a controller is provided having a memory that stores the series of measurements and having a processor that combines the data from the different measurements to calculate the concentrations of airborne particles as a function of their aerodynamic particle sizes.

Preferably also, dynamic calibration is carried out before measurements of unknown concentrations of particles are taken. The calibration may include the operation of the rotating element at each of its different settings, such as by increasing its rotary speed through a sequence of predetermined rotational speeds, and collecting or otherwise measuring the total of the particles or the numeric distributions of the remaining particles of each of the aerodynamic size distributions as the parameters or settings of the rotating element are varied. Determination of the aerodynamic particle size distribution may be made by use of a relatively inexpensive sensing device, such as an optical single particle counter, an aerosol photometer, or any other aerosol sensor that responds to a specific property of the aerosol particles such as mass, fluorescence, magnetism, radioactivity, etc.

In one preferred method of the present invention, airborne particles are drawn through an aerodynamic cut device which continuously or intermittently changes the aerodynamic cut of the particles entering an aerosol sensor. Aerosol sensing may include optical sensing performed, for example, by optical single particle size spectrometry or by aerosol photometry. The aerodynamic cut may be achieved by rotating the rotating element to centrifugally remove particles larger than a specific size to the inner wall of the housing containing the rotating element. Continuously changing the aerodynamic cut has the advantage of taking less time, since the voltage signal of the aerosol sensor can be related to the operational characteristics of the aerodynamic cut device through consideration of the time it takes for the aerosol particles to move from the aerodynamic cut device to the sensing element of the aerosol sensor.

In the preferred embodiment of the invention, the rotating element is configured to allow the aerosol to remain in the cut device for sufficient time to allow particles that are to be extracted by the cut device to be efficiently removed from the aerosol. This is achieved by restricting the outlet from the apparatus so as to prevent a high flow rate of aerosol through the apparatus due to the rotation of the rotating element, particularly when the rotating element is rotating at higher rotational speeds. Further, a pump is preferably provided at the outlet of the apparatus to facilitate flow of aerosol through the apparatus at low rotational speeds of the rotating element and when the element is not rotating. Preferably, outlet flow restriction and separate pumping are coordinated to provide a constant rate of aerosol flow through the apparatus.

In the preferred method, the measurements are first taken with the rotating element of the aerodynamic cut device not rotating. When the rotating element is stationary and an optical single particle counter is used as a sensor, the sensor records the aerosol particle counts in specific "optical particle diameter" ranges. The amount of light scattered or absorbed by a particle depends on the optical characteristics of the particle. Such "optical particle diameter" generally does not correspond to the "aerodynamic particle diameter".

Calibration to aerodynamic particle size of an apparatus that employs a single particle counter as a sensor is performed while a constant aerosol particle size distribution is maintained, with the aerodynamic cut device continuously or intermittently increasing its rotational speed as a series of measurements are taken. Each rotational speed corresponds to a specific aerodynamic cut size. In the preferred embodiments of the invention, the aerodynamic particle size of the changing aerodynamic cut decreases as the rotational speed increases. In this way, the optical particle size can be related to a corresponding aerodynamic particle size for the aerosol being measured. Once an optical single particle counter is calibrated relative to aerodynamic particle size for a specific aerosol environment, the aerodynamic cut device can be removed and the optical single particle counter can be operated alone as long as the material characteristics of the aerosol particles and the determined size distribution of particles in the aerosol do not change substantially.

In a preferred embodiment of the invention in which an aerosol photometer is used as the aerosol sensor in the apparatus, the aerodynamic cut device becomes an integral part of the photometer, effectively turning the aerosol photometer into an aerosol size spectrometer. With such an apparatus, at the beginning of a measurement cycle, a measurement is made with the rotating element in the aerodynamic cut device not rotating. Thus, the aerosol photometer output from a measurement of the aerosol entering the aerosol photometer at the beginning of the measurement cycle corresponds to the entire aerosol cloud passing into the apparatus. As the rotating element in the aerodynamic cut device increases its rotational speed, the aerosol photometer output is reduced by the amount of aerosol particles removed in the aerodynamic cut device. Thus, the difference in signal output obtained when increasing the speed of rotation of the rotating element corresponds to the aerosol particles removed in the aerodynamic particle size range defined by two rotating speeds, and is calculated by subtracting the two stored measurements with a controller. For calibration, the aerosol particles that have passed through the aerosol photometer can be collected on a filter, and the particle count, surface area, volume or mass of particles deposited on the filter can be related to the photometer signals.

With this invention, higher aerosol concentrations can be measured than with the more complex and expensive "time of flight" method, because in the "time of flight" method the processing time for each particle is much longer. When aerosol photometry or dynamic aerosol mass sensing is used for the aerosol sensing, the aerosol flow rate can be much higher than in the "time of flight" method. Thus, a much larger volume of air can be analyzed as to its aerodynamic particle concentration in specific aerodynamic size ranges.

Thus, advantages of the present invention include provision of an inexpensive apparatus and method for calibrating an optical single particle counter with respect to the aerodynamic particle sizes of the aerosol particles being sampled. Embodiments of the invention are effective when using an optical single particle counter. The method can be used as an integral part of an aerosol photometer or aerosol mass sensor so that the output of the aerosol photometer or aerosol mass sensor can be related to specific aerodynamic particle sizes, thus turning the aerosol photometer or aerosol mass sensor into an aerodynamic particle size spectrometer.

Another advantage of the present invention is the ability to measure higher concentrations of aerosol particles than is possible with the more complex and expensive "time of flight" method. A further advantage of the invention is the ability to measure a larger volume of aerosol particles per unit of time than is possible with the more complex and expensive "time of flight" method.

These and other objectives and advantages of the present invention will be more readily apparent from the following detailed description of the of the preferred embodiments of the invention.

Figure 2A:
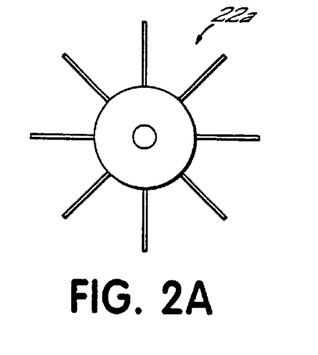
FIGS. 2A–2D are partial cross-sectional views along the line 2—2 of FIG. 1 illustrating alternative configurations of rotating elements of the cut device.
Figure 2B:
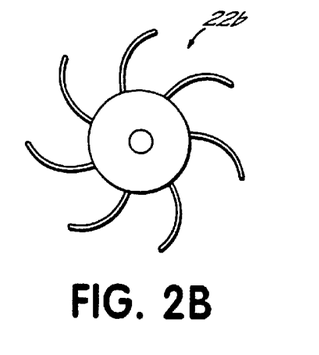
Figure 2C:
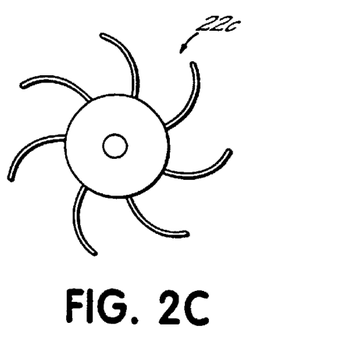
Figure 2D:
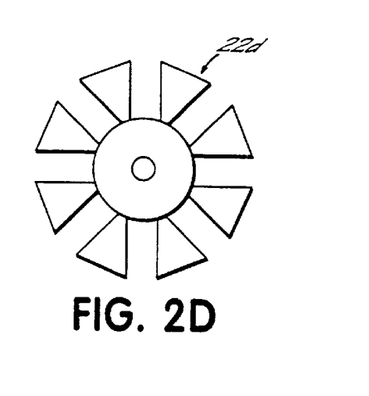
Figure 3A:
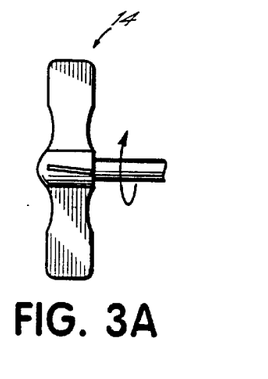
FIGS. 3A and 3B are diagrams of cut device variable pitch rotating element alternatives to the elements of FIGS. 2A—2D.
Figure 3B:
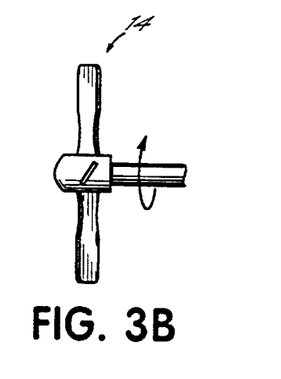
Figure 4A:
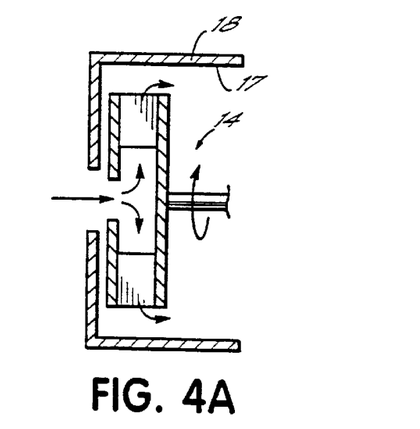
FIGS. 4A and 4B are diagrams of further cut device variable configuration rotating element alternatives to those of FIGS. 3A–3B.
Figure 4B:
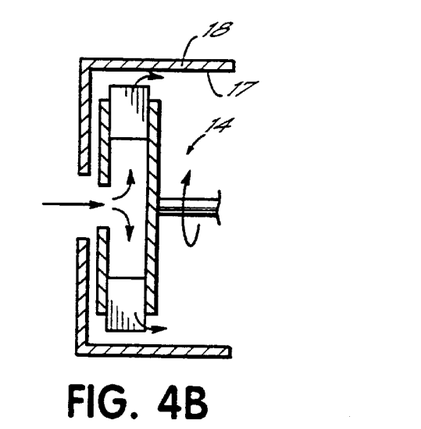

The rotating element 14 may include one or more disc or propeller blades mounted on a rotating shaft, or an impeller with radial, forward-curved or backward-curved blades, or an impeller with constant cross-section radial passages as illustrated in FIGS. 2A–2D. Furthermore, variable pitch blades as illustrated in FIGS. 3A and 3B may be used in an axial fan configuration. FIG. 3A illustrates such an axial fan with the blades aligned parallel to the axis of rotation, therefore providing maximum particle removal at a given RPM. In FIG. 3B, the same blades are aligned in a plane perpendicular to the axis of rotation, providing minimum particle removal at a given RPM. The angles can be made to vary between these two extremes to provide control of the particle removal of the cut device 12. FIGS. 4A and 4B illustrate blades of the rotary element 14 placed at different radial positions relative to the peripheral inner wall 17 of the housing 18 of the cut device 12. The configuration of FIG. 4B with the blades closer to the wall 17 typically results in a lower particle size cut because more particles are removed from the aerosol. Radial in-out adjustability of the blades can be provided by making the blades moveable on the rotary element 14 and providing a suitable adjustment mechanism.

Figure 1:
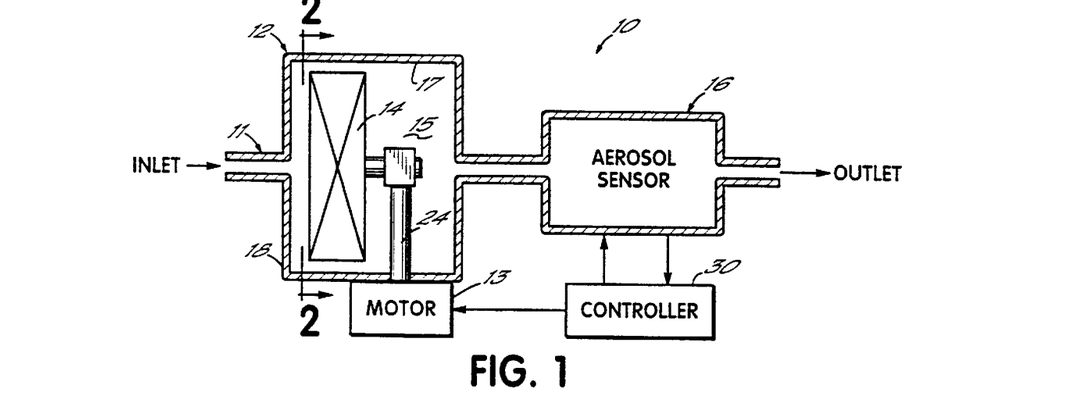
FIG. 1 is a schematic diagram of an aerodynamic particle size analysis apparatus according to principles of the present invention.

As seen more particularly in FIG. 1, the preferred embodiment of the invention includes an aerodynamic cut device 12, aerosol sensor 16, and a controller 30. The controller 30 is programmed and operable to perform control, monitoring and data storage functions and to process the data for analysis. The aerodynamic cut device 12 is controlled by the controller 30 so as to continuously or intermittently change the aerodynamic cut of aerosol entering through the inlet 11 and proceeding to the aerosol sensor 16. Preferably, the cut is changed by stepping the cut progressively through discrete selected cut sizes or by changing the cut continuously. The cut device 12 preferably removes particles larger than the aerodynamic cut size of the selected cut so that mostly only particles below the aerodynamic cut size enter the aerosol sensor 16.

Figure 1A:
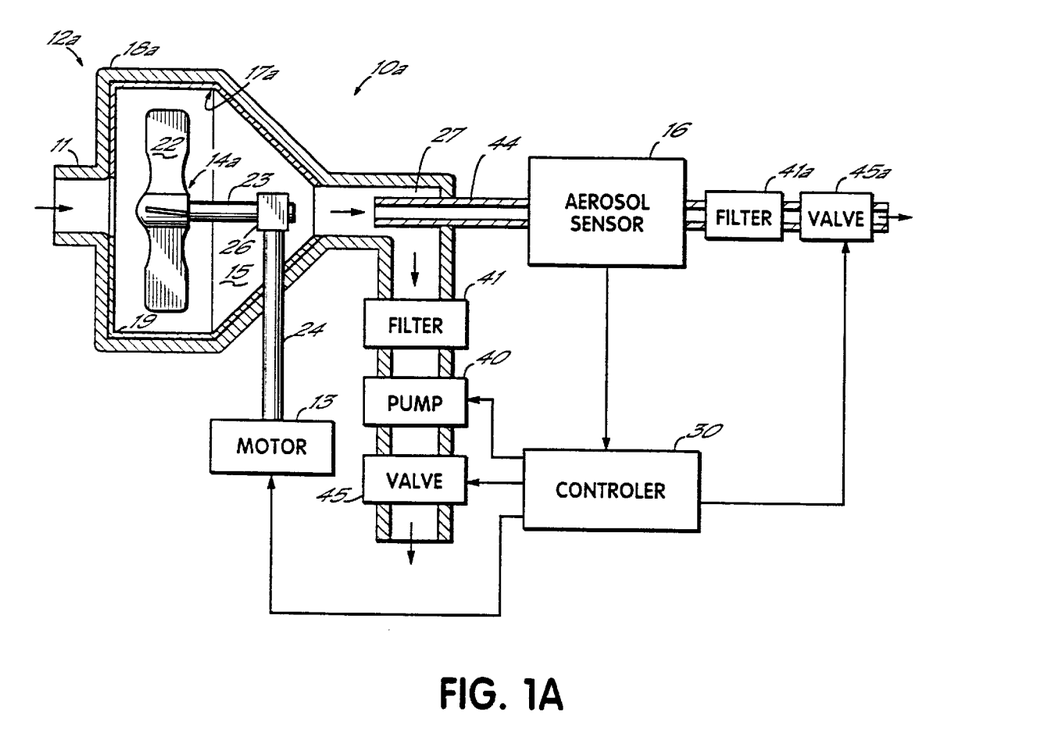
FIG. 1A is a schematic diagram of one embodiment of the apparatus of FIG. 1.

One embodiment of an apparatus 10a is illustrated in FIG. 1A. In the apparatus 10a, an aerosol to be analyzed is drawn into the aerodynamic cut device 10a through inlet 11 which can be of any design compatible with sampling the aerosol particles under consideration. The aerosol to be analyzed passes through this inlet 11 into the housing 18a of the aerodynamic cut device 12a. The device 12a contains a rotary element 14a in the form of an axial fan which is a propeller-like impeller. Impellers of the tube-axial or vane-axial types are also suitable alternatives, and may be designed to propel aerosol through the apparatus 10 or merely to centrifugally move the airborne particles for selective removal, relying in whole or in part on a separate pump or fan to move the aerosol through the apparatus 10. With the illustrated rotary element 14a, blades 22 are fixed to and extend radially from a shaft 23 and rotate at a speed that can be changed, either continuously through an infinite number of settings or intermittently among discrete speed settings from zero to a high number of revolutions per minute (RPM). The RPM depends on the aerodynamic cut size desired, and the size and design of the blades 22. The blades 22 are rotated by motor 13 whose drive shaft 24 moves shaft 23 through coupling 26. Coupling 26 is an example of how the motor 13 can rotate the blades 22. Other means of coupling can be used. The speed of the motor 13 is preferably variable and controlled by the controller 30. The variation in the speed of the rotary element 14a is preferably the mechanism for the selective variation of aerodynamic cut setting of the cut device 12a.

To enhance the ability of the cut device to remove particles from the aerosol, the inside wall 17a of the housing may have attached to it a coating of sticky substance 19 whose purpose is to retain the particles that are removed from the aerosol flow to the inner wall 17a of the housing 18a by rotation of the blades 22. Sticky substance 19 may be a material such as oil or other adhesive material and may be applied directly to the inner wall 17a of the housing 18a. Sticky substance 19 may also be a removable insert with an adhesive coating on the side facing the blades 22. The blades 22 may be made of or coated with a non-sticky material such as silicone or TEFLON to reduce particle adhesion to the blades 22. Alternatively, the blades may be made sticky to exploit rather than inhibit removal of particles by the blades. The rotary element 14a may have radial blades 22a, backward-curved blades 22b, forward-curved blades 22c or a constant cross-section radial passage impeller 22d, as illustrated respectively in FIGS. 2A–2D, or airfoil blades (not shown). Blade configuration can affect the "sharpness" of the aerodynamic cut by the cut device 12. For instance, the air velocity in FIG. 2D is quite uniform across the cross-section at a given radial position in the constant cross-section impeller shown. Thus, each constant cross-section passage forms a moving impaction nozzle. The more uniform the aerosol particle velocity in leaving the impeller, the greater the "sharpness" of the aerodynamic cut.

The housing 18a preferably has an outlet to which is attached a flow splitter 27 having a first branch that connects to the aerosol sensor 16 and a second branch that connects to an exhaust pump 40. The pump 40 provides the main propulsion of aerosol through the apparatus 10a. An optional filter 41 is also inserted in the second branch upstream of pump 40. An optional filter 41a may also be provided at the outlet of the aerosol sensor 16. Pump 40 is preferably variable and controlled by the controller 30, which is programmed to operate 20 the pump 40 so as to maintain a desired flow rate, such as a constant flow rate, through the apparatus 10a. The flow splitter 27, pump 40 and filters 41,41a may be used with other embodiments of the apparatus 10 described herein.

In addition or in the alternative to the pump 40, flow control through the various embodiments of the apparatus 10 may be controlled by the placement of a flow restriction valve 45 in the second branch of the flow splitter 27. The valve 45 provides the ability to restrict the flow through the cut device 12 so that the aerosol can be made to remain longer in the cut device 12, which facilitates the extraction of smaller particles from the aerosol by the cut device 12. The valve 45 may be provided in series with a pump 40 or in systems 10 that do not have a pump 40 where, for example, the rotary element 14 of the cut device 12 provides the propulsion force to move the aerosol through the cut device 12. A valve 45a may similarly be provided at the outlet of the aerosol sensor 16, particularly in systems that do not include a flow splitter 27, to restrict the flow through the cut device 12 of apparatus 10. Valves 45 and 45a may be controlled in coordination with the motor 13 where the rotary element 14 is rotated at different speeds or with blade pitch variation. With the ability provided by the flow restrictors 45,45a to cause the aerosol to remain longer in the cut device 12, the ability to remove smaller particles is increased, which allows the cut size to be varied over a wider range, for example, over a range of 30 to 1.

The flow rate of the aerosol entering the aerodynamic cut device 10a is equal to the sum of the flow rates through pump 40 and through an inlet 44 of the aerosol sensor 16. In some circumstances, the flow splitter 27 can be eliminated so that the aerosol sensor 16 is directly coupled to the exit port of the aerodynamic cut device 12. In that case, the volumetric flow rate entering the aerosol sensor 16 through its inlet 44 equals the volumetric flow rate entering the aerodynamic cut device 12 through the inlet 11. Sensing of the airborne particles may be performed by sensors 16 that perform optical single particle size spectrometry or aerosol photometry or by other aerosol sensor devices.

Figures 1B, 1C, 1D, 1E:
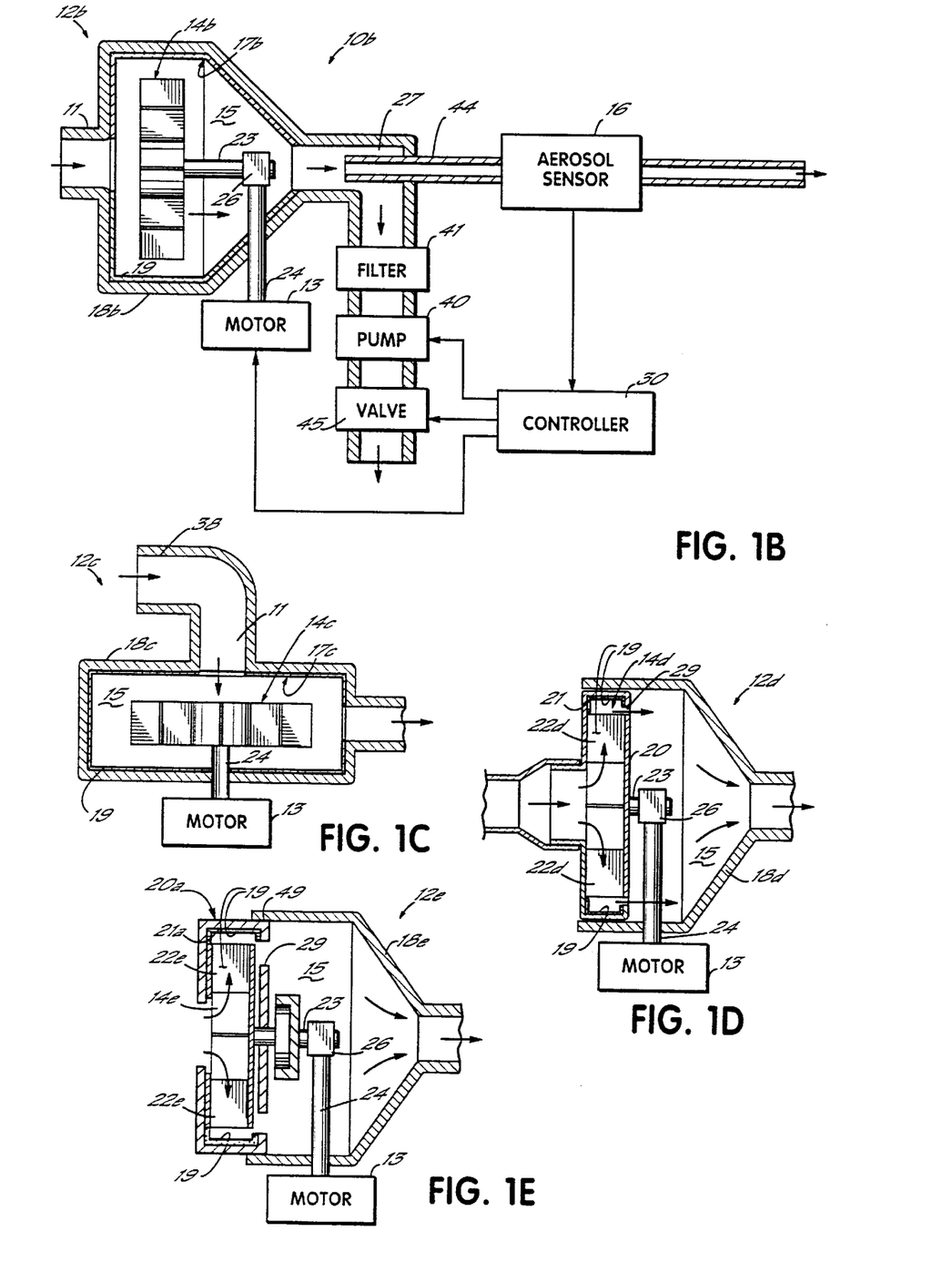
FIG. 1B is a schematic diagram of a portion of FIG. 1 illustrating an alternative to the cut device portion of the apparatus of FIG. 1A.
FIG. 1C is a schematic diagram of a portion of FIG. 1 illustrating another alternative to the cut device portion of the apparatus of FIGS. 1A and 1B.
FIG. 1D is a schematic diagram of a portion of FIG. 1 illustrating a further alternative to the cut device portion of the apparatus of FIGS. 1A–1C.
FIG. 1E is a schematic diagram of a portion of FIG. 1 illustrating a still further alternative to the cut device portion of the apparatus of FIGS. 1A–1D.

The blades 22 of FIG. 1A may be replaced by a centrifugal fan type rotary element 14b of the alternative cut device 12b illustrated in FIG. 1B. All such rotating element configurations can be effective for centrifugally removing aerosol particles larger than the desired aerodynamic cut sizes by use of the aerodynamic cut device 12a. Other elements and their functions may be similar to those shown in FIG. 1B.

In FIG. 1C, a less preferred though useable centrifugal fan type rotary element 14c is provided having either radial, forward-curved, backward-curved or constant cross-section blades similar to the rotary element 14b shown in FIG. 1B. In the illustration of FIG. 1C, the exit aerosol flow from the aerodynamic cut device 12c is perpendicular to the incoming aerosol flow. In this case, the motor 13 may be attached directly to shaft 23 without use of a coupling. All other elements and their functions may be similar to those of the embodiment of FIG. 1B. An optional inlet extension 38 with a gradual ninety degree bend can be attached to inlet 11 of the aerosol cut device 12c, to permit the aerosol to be sampled in the same direction as the inlet axis of the aerosol sensor 16.

In FIG. 1D, rotary element 14d is provided with blades 22d carried on the interior of enclosure 20 which rotates as an integral part of the rotary element 14d. The enclosure 20 serves as a collector and has an interior surface 21 on which, along with the surfaces of the blades 22d, collect the particles which the cut device 12 removes from the aerosol passing therethrough. The enclosure 20 collects the extracted particles more effectively than in many cut devices 12 of the type described above in which particles are collected on the inside 17 of a stationary housing 18. In rotary enclosures 20, exit holes 29 are provided in the end wall of the enclosure 20 near but slightly spaced from the peripheral surface which is the primary collector surface 21, to allow flow of aerosol containing the airborne particles that survive the cut out of the enclosure 20 to the exit of the cut device 12d.

With the embodiment of FIG. 1D, the rotary element 14d with the impeller or assembly of blades 22d and enclosure-collector 20 are rotated at progressively various speeds under the control of controller 30. This assembly has the advantages of easy removal for cleaning or replacement of both the enclosure-collector 20 and blades 22d as well as for replacement with a rotary element 14 that is differently designed, which may be desirable when the nature of the aerosol to be analyzed is changed. The rotary element assembly 14d can be made to be disposable rather than to be cleaned.

FIG. 1E illustrates a cut device 12e having a rotating element 14e having a rotating enclosure 20a that serves as a collector similar to the that of FIG. 1D, with the additional feature that the entire rotating element 14e, which includes blades 22e and the enclosure 20a which contains all of the surfaces on which the extracted particles deposit, is removeable as a unit for replacement or cleaning. The enclosure-collector 20a, which rotates at the same speed as the rest of the rotating element 14e, is sealed to the housing 18e of the cut device 14e through seals or other sealing members 49. Further, the coupling to the motor can be by screws or other mechanical fasteners (not shown), by magnetic attachment, or in some other way that leaves the rotating element assembly 14e easily disconnectable from housing 18e so that the entire assembly of the rotating element 14e can be removed for cleaning or replacement. When removed, if the collecting surfaces are to be cleaned, the cleaning can be carried out by removal of the sticky surface material or by immersion of the rotating element assembly 14e in solvents or cleaning liquids. The element assembly 14e can also be cleaned along with other passages of the apparatus 10 by blowing higher than normal air through the cut device 12. Where a flow restriction valve 45 is provided, such a valve should be fully opened and the pump 40 operated at high volume. Alternatively, an external high volume pump may be applied to circulate the cleaning air through the apparatus 10.

In certain preferred embodiments of the invention, aerosol sensing is performed by sensor 16 by aerosol photometry. An aerosol photometer measures the amount of light scattered from a cloud of particles. The light scattering signal resulting from light illumination of a particle cloud depends primarily on the optical properties and the size of each particle in the view volume of the aerosol photometer. Thus, a standard aerosol photometer does not give an output signal relative to particle size. When an-aerosol photometer is used for the aerosol sensor, the aerodynamic cut device 12 effectively turns the aerosol photometer into an aerosol size spectrometer, as the cut is varied and a series of measurements are taken. The aerosol photometer output is related to aerodynamic particle size while the aerodynamic cut device 12 continuously or intermittently increases its rotational speed such that each rotational speed corresponds to a specific aerodynamic cut size. The aerodynamic particle size of this aerodynamic cut decreases as the rotational speed of the rotating element 14 increases. In order to achieve a wide range of particle cut sizes, several cut devices 12 of the same or different types or operating characteristics can be connected in parallel or in series.

Figure 5:
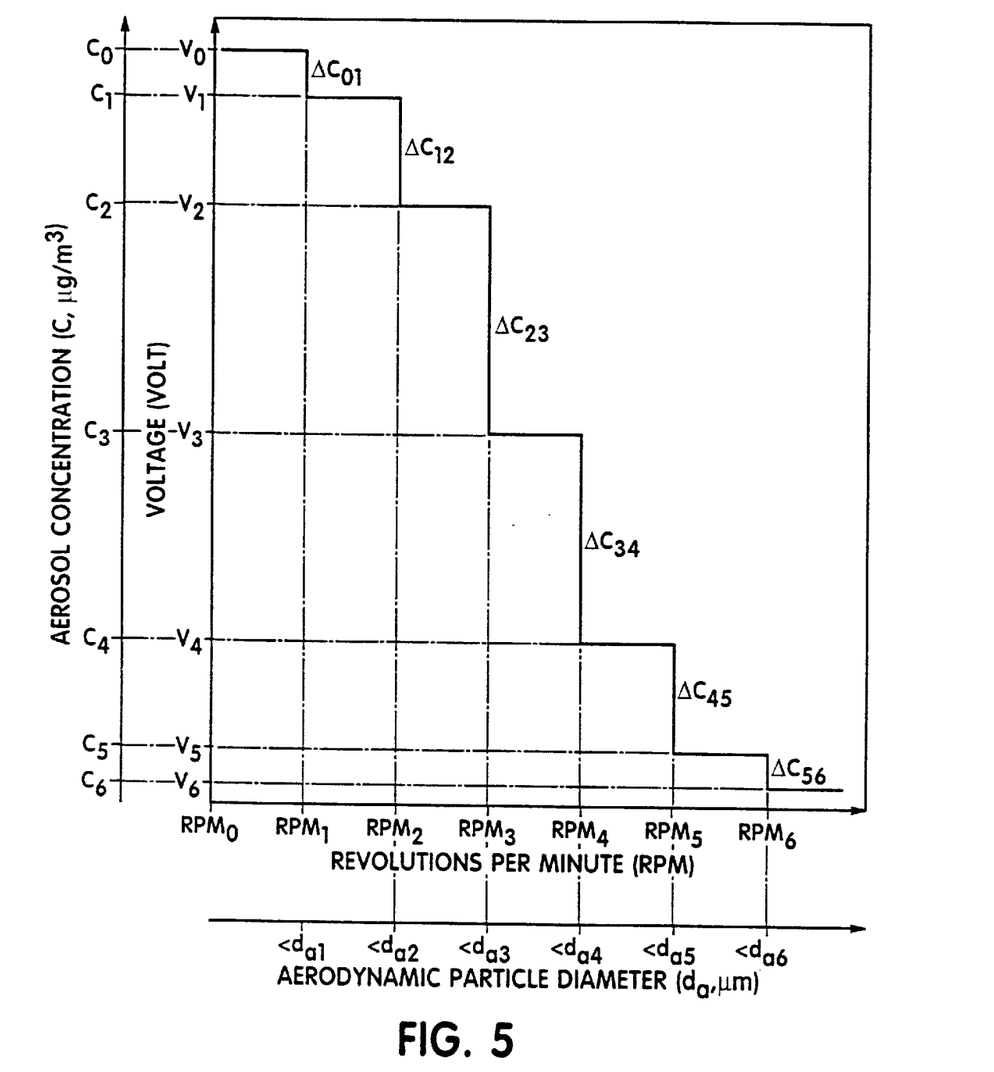
FIG. 5 is a graphical representation of typical raw and processed output data signals from an aerosol photometer or mass type aerosol sensor of an apparatus of FIG. 1.

Typical output signals from an aerosol photometer, when used with the aerodynamic cut device 12 are shown in FIG. 5. At the beginning of a measurement cycle, the rotating element 14 in the aerodynamic cut device 12 is non-rotating. Thus, it is rotating at zero revolutions per minute, i.e., RPM =0. This value is shown as $RPM_0$ on the abscissa of FIG. 5 and results in a light scattering signal from the entire particle cloud, exemplified as voltage $V_0$ on the ordinate of FIG. 5. The illustration of FIG. 5 is for intermittent increases in RPM of rotating element 14. When the rotating element 14 is set to $RPM_1 > 0$, the photometer voltage is reduced to $V_1$, if particles larger than the aerodynamic cut size at $RPM_1$, are present in the aerosol cloud entering the aerodynamic cut device 12. Thus, most of the remaining aerosol particles are less than aerodynamic particle diameter $d_{a1}$ in size, as shown on the second abscissa in FIG. 5. The relationship between RPM and aerodynamic particle diameter $d_a$ can be established theoretically, or experimentally by calibration with spherical test particles of known particle density, such as polystyrene latex (PSL) spheres. Subsequent increases in RPM decrease the aerodynamic cut size and correspondingly the photometer signal, if particles are removed by the aerodynamic cut device 12. The voltage signals from an aerosol mass sensor or other aerosol sensor responding to a property of the aerosol particles, such as fluorescence or radioactivity, are related to aerodynamic cut in a similar way.

Figure 6:
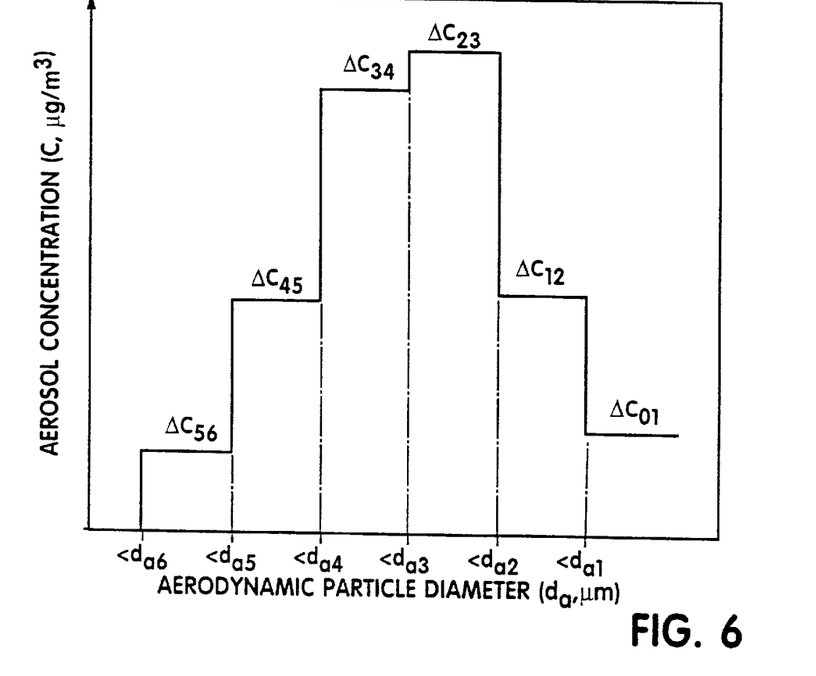
FIG. 6 is a graphical representation of an output display of an aerodynamic particle size distribution output by the aerosol photometer or mass sensor of the apparatus of FIG. 1 operating as an aerodynamic particle size spectrometer.

One of the ways in which the decrease in photometer output voltage in a specific aerodynamic particle size range can be related to the particle count or particle mass in that aerodynamic particle size range is as follows. While maintaining a constant aerosol flow rate upstream of inlet 11 to the aerodynamic cut device 12, the aerosol particles that are not removed by the aerodynamic cut device 12 are collected on a filter. Conventional aerosol photometers generally allow insertion of a filter downstream of a photometric sensor. The difference in particle count or particle mass on the filters is then attributed to the difference in photometer voltage signal for the corresponding aerodynamic particle size range. Thus, the output signals of the aerosol photometer are calibrated relative to the rotational speed of the rotating element 14 of the cut device 12. This results in indications of the aerosol concentration C as a function of equivalent aerodynamic particle diameter $d_a$, as shown in FIG. 5. FIG. 5 exemplifies the aerosol concentration in $\mu g$ (micrograms) of particle mass per m$^3$ (cubic meter) of air or aerosol volume sampled. Aerosol photometer signal $V_0$ corresponds to aerosol concentration $C_0$, $V_1$ to $C_1$, $V_2$ to $C_2$, etc., as shown on the two ordinates in FIG. 5. The difference in aerosol concentration $\Delta C$ for a specific aerodynamic particle size range is also shown in FIG. 5. For instance, $\Delta C_{23}$ is the aerosol concentration in the aerodynamic particle size range between aerodynamic particle diameter $d_{a2}$ and aerodynamic particle diameter $d_{a3}$. The aerosol concentration C in specific aerodynamic particle size ranges can then be plotted as a function of aerodynamic particle diameter $d_a$, as shown in FIG. 6. FIG. 6 is a typical output signal from an aerosol photometer when the invented method turns the aerosol photometer into an aerosol size spectrometer. A similar output results from the use of an aerosol mass sensor or another aerosol sensor responding to an aerosol property.

Another method that can be used for optical sensing is optical single particle size spectrometry. In an optical single particle counter, the optical view volume is very small so that ideally only one particle at a time passes through the illuminated volume, resulting in a pulse of scattered light that is recorded by a sensor. The strength of each signal depends on the optical characteristics and the size of the particle passing through the view volume. An optical single particle counter is typically particle-size calibrated with spherical test particles of known optical characteristics, such as PSL spheres. The particle size distribution is then recorded as a function of "optical particle diameter".

When an optical single particle counter is used as the aerosol sensor 16 as part of the method described in this invention, the optical single particle counter is first operated while the rotating element 14 in the aerodynamic cut device 12 is not rotating. At that time, the optical single particle counter records the aerosol concentration in specific "optical particle diameter" ranges. Since the amount of light scattered or absorbed by a particle depends on its optical characteristics, the "optical particle diameter" generally does not correspond to the "aerodynamic particle diameter". The calibration relative to aerodynamic particle size is performed in this invention while a constant aerosol particle size distribution is maintained, and the aerodynamic cut device continuously or intermittently increases its rotational speed. Each rotational speed corresponds to a specific aerodynamic cut size. The aerodynamic particle size of this aerodynamic cut decreases as the speed increases. Thus, the optical particle size is related to its equivalent aerodynamic particle size for the aerosol being measured. Once an optical single particle counter is calibrated relative to aerodynamic particle size for a specific aerosol environment, the aerodynamic cut device can be removed and the optical single particle counter can be operated alone as long as the material characteristics of the aerosol particles do not change substantially.

Figure 7A:
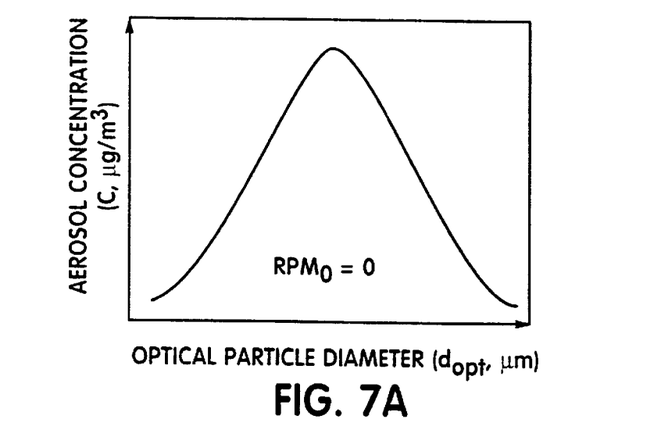
FIGS. 7A–7C are graphical representations of typical particle size distributions recorded by an optical single particle size spectrometer type aerosol sensor at various aerodynamic particle size cut settings of the cut device of the apparatus of FIG. 1.
Figure 7B:
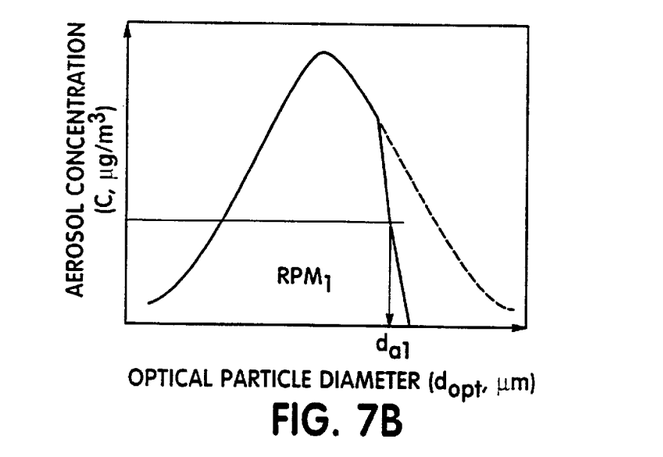
Figure 7C:
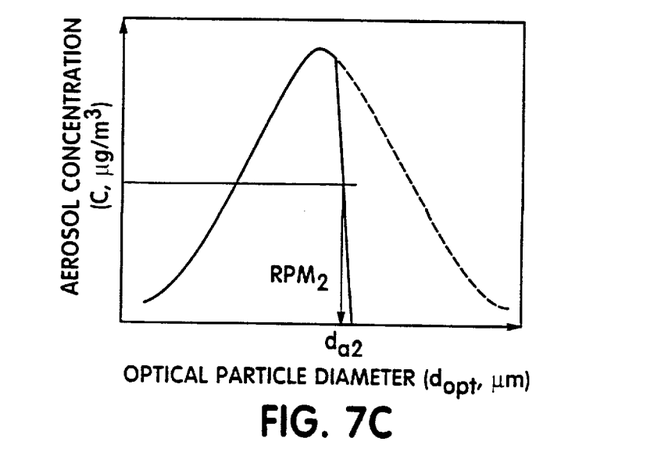

In this invention, the method for calibrating the optical single particle counter with respect to aerodynamic particle size is illustrated in FIGS. 7A–7C. At the beginning of the calibration cycle, the optical single particle counter records the aerosol concentration as a function of the optical particle diameter $d_{opt}$ while the rotating element 14 in the aerodynamic cut device 12 is not rotating. FIG. 7A illustrates a typical particle size distribution measured at $RPM_0 = 0$. The curve in FIG. 7A is fitted to the aerosol concentration data in specific optical particle size channels. The aerosol concentration is exemplified as the number of aerosol particles per m$^3$ of air volume sampled.

When the rotating element 14 in aerodynamic cut device 12 is rotated at $RPM_1 > 0$, the particles larger than the aerodynamic cut size corresponding to $RPM_1$ are removed by the aerodynamic cut device, and the particle size distribution is truncated, as illustrated in FIG. 7B. The optical particle diameter at which the truncated part of the particle size distribution is half of its original value can be defined as the aerodynamic cut diameter $d_{a1}$ corresponding to $RPM_1$. Other parts of the truncated curve may also be used to define the aerodynamic cut. As the rotational speed of the rotating element 14 is further increased to $RPM_2$, the particle size distribution curve may be truncated further, as shown in FIG. 7C.

Figure 8:
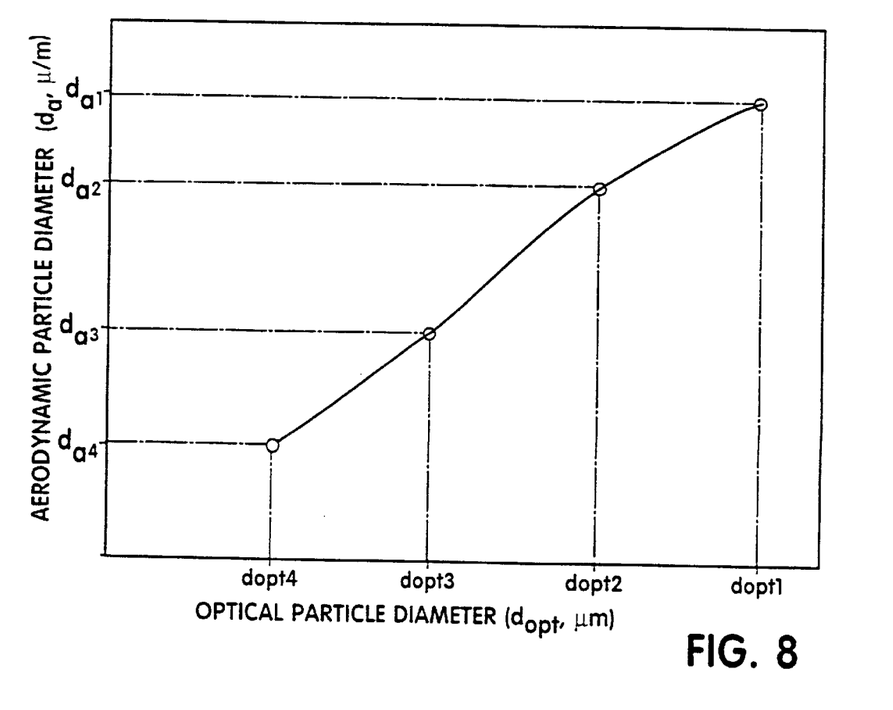
FIG. 8 is a graphical representation of the relation between aerodynamic particle size and optical particle size for an optical single particle counter in the apparatus of FIG. 1 sampling an aerosol environment.

The relationship between the optical particle diameter $d_{opt}$ at which the aerodynamic cut device 12 removes essentially all particles above a specific aerodynamic particle diameter $d_a$ is exemplified in FIG. 8. The calibration curve for the data in FIG. 8 is then entered into the memory of the optical single particle counter or the controller 30. Subsequent measurements of the aerodynamic particle size distribution are then made while the rotating element 14 in the aerodynamic cut device 12 is non-rotating, or the entire aerodynamic cut device 12 is removed from the inlet of the optical single particle counter. Renewed calibration is performed to confirm the validity of the previous one, or when the optical characteristics of the aerosol particles being sampled are considered to have changed significantly.

There are certain aspects of a calibration procedure that are preferably applied to all of the aerosol sensors 16 useful with the preferred embodiments of the present invention. This is true whether the sensor is an aerosol photometer which gives a light scattering signal from a light shown onto an, aerosol cloud passing through the sensor 16, whether it is a mass sensor, for example, that gives a voltage or other electronic signal relative to the amount of mass collected on a surface, or whether it is any other sensor that gives a response to a property (e.g. magnetism, radioactivity, fluorescence, number of particles, etc.) that changes in the aerosol sensor in response to the particle cut size determined by the setting of the cut device 12.

The calibration procedure should include the (1) dispersing into the apparatus 10 test aerosols of uniform concentration made up of, for example, spherical polystyrene latex (PSL) particles of known particle size and particle density, then calculating for each particle diameter $d_p$ and particle density $\rho_p$ the aerodynamic particle diameter $d_a$ as $d_a = d_p (\rho_p)^{1/2}$. Then, (2) while the rotary element 14 is stationary and the flow through the device is at some controlled flow rate $Q_0$, recording the signal given by the aerosol sensor. This signal corresponds to the case where all the particles reach the aerosol sensor, without any being removed by the operation of the cut device 12. This is the reference signal to which all subsequent signals for specific RPM's and Q's are related. Then, (3) with the rotary element 14 rotated to a first of a sequence of rotational speeds and with the flow rate maintained at the controlled flow rate of $Q_0$, recording the signal from the aerosol sensor again. Then, the flow is restricted to a lower flow rate $Q_1$, by adjustment of the pump 40 or flow restriction valve 45, so that the aerosol particles have longer residence time in the preclassifier, resulting in more particle removal, recording the signal from the aerosol sensor again. Then, (4) while keeping the RPM of the rotary element constant, increasing the flow restriction to a still lower flow rate of $Q_2$, and recording the sensor output signal. Then, the RPM of the rotary element 14 should be sequentially increased, and with each increase in RPM, steps (2) through (4) should be repeated.

Figure 9:
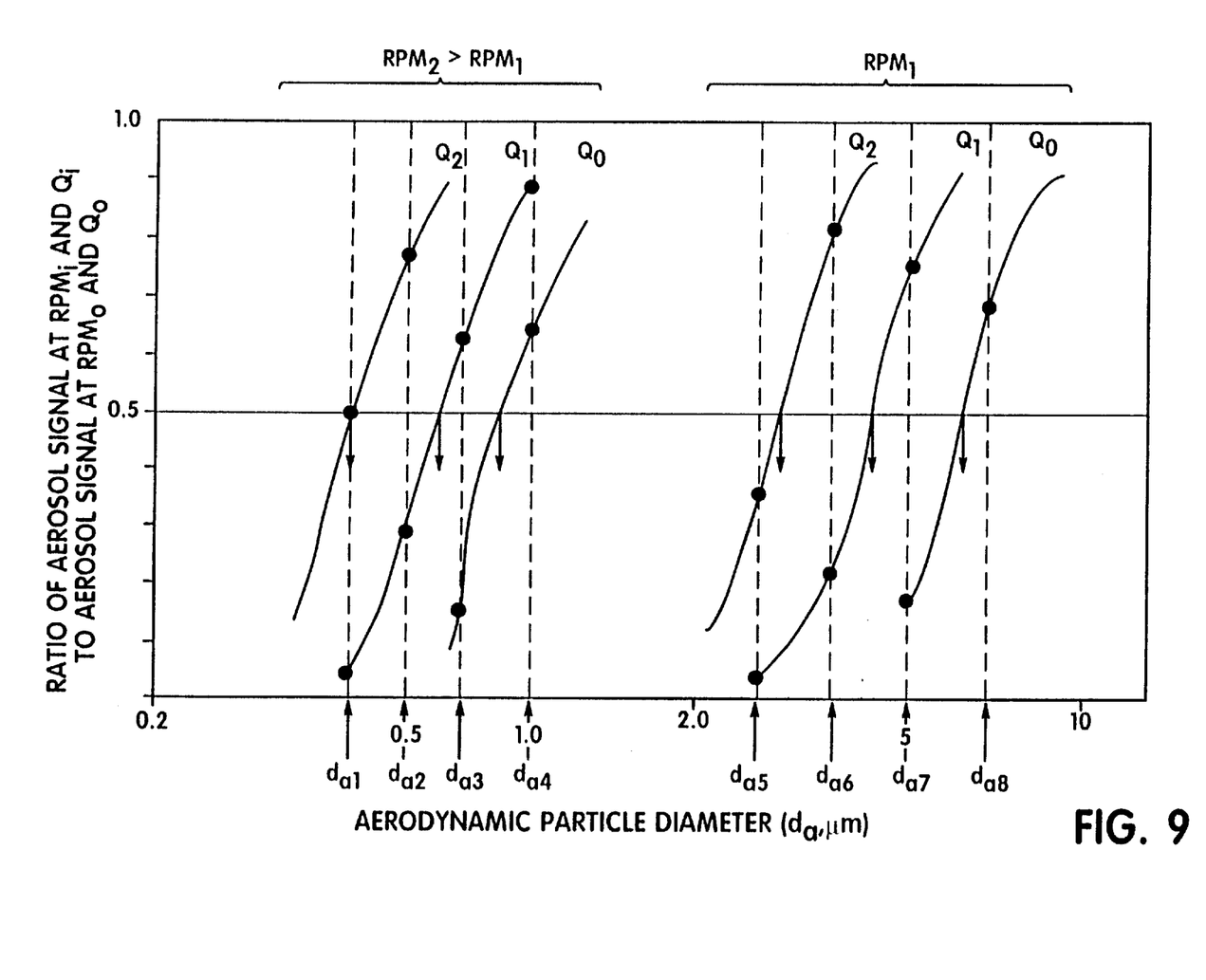
FIG. 9 is a graphical representation of the calibration curves at various a centrifugally remove particles larger than a specific size from the aerosol that enters the apparatus 10 through the inlet 11. Typically, the cut is made by removing particles larger than the aerodynamic cut to an inner wall 17 of a fixed housing 18 of the cut device 12 of the apparatus 10 of FIG. 1. For example, the removed particles are collected on walls 17a–17c of a fixed housing 18a–18c containing the rotating elements 14a–14c, as respectively illustrated in embodiments 10a–10c of FIGS. 1A–1C, or onto the inner walls 21,21a of enclosures 20,20a that rotate with the rotating elements 14d–14e, as respectively illustrated in the cut devices 12d,12e of the embodiments of FIGS. 1D and 1E. Some particles are also removed to the blades of the rotating elements, which can be coated with sticky substances in certain applications where it is desired to exploit such particle removal.

The preferred calibration procedure results in calibration curves that are exemplified in FIG. 9 for each specific aerodynamic particle size. This is plotted as a ratio of aerosol signal measurements at various $Q_i$ and RPM; to the signal at $RPM_0$ and $Q_0$. The aerodynamic particle cut size $d_{50}$ is defined as the aerodynamic particle size at which 50% of the particles, as recorded at $RPM_0$ and $Q_0$, are removed. The desired particle cuts are affected by changing the RPM or Q or both. In FIG. 9, the calibration aerosol particles $d_{a5}$ through $d_{a8}$ yield aerodynamic cut size information for operation of the rotating element 14 at $RPM_1$. Correspondingly, in FIG. 9, the calibration aerosol particles $d_{a1}$ through $d_{a4}$ yield aerodynamic cut size information for operation of the rotating element 14 at $RPM_2 > RPM_1$.

An alternative calibration procedure is to use a calibrated aerodynamic particle size spectrometer that is calibrated by a similar procedure as shown above and relating the recorded aerosol sensor output signals to the aerodynamic particle sizes of the reference aerodynamic particle size spectrometer. This procedure is somewhat faster to perform.

With the present invention, higher aerosol concentrations can be measured than with the more complex and expensive "time of flight" method. In the "time of flight" method, the aerodynamic particle size distribution is determined in situ by accelerating the aerosol particles in a nozzle and then measuring the "time of flight" of each particle between two points. In a nozzle or other acceleration field, aerodynamic drag accelerates large particles to a lesser extent than small particles. Thus, in an acceleration field, the time of flight between two points is longer for large particles than for small particles. The difference is caused by the difference in aerodynamic drag. Thus, the "time of flight" method determines the particle size distribution relative to aerodynamic particle size. Since the time of flight in these devices is usually longer than the single light scattering pulse in an optical single particle counter, the single particle counter can generally be operated at higher aerosol concentrations.

When aerosol photometry, aerosol mass sensing or any other method of recording an aerosol property is used for the aerosol sensing, the aerosol flow rate can be much higher than in the "time of flight" method. Thus, a much larger volume of air can be analyzed as to its aerodynamic particle concentration in specific aerodynamic size ranges.

Those skilled in the art will appreciate that the applications of the present invention described herein are varied, and that the invention is described in preferred embodiments. Accordingly, additions and modifications can be made without departing from the principles of the invention. Accordingly, the following is claimed.

What is claimed is:

1. A method for determining the concentrations, in an aerosol that includes air and airborne particles, of the airborne particles as a function of their aerodynamic particle sizes. the method comprising the steps of:
   flowing aerosol into an aerodynamic cut device having a rotating element that at successively higher rotational speeds makes aerodynamic cuts at successively smaller aerodynamic particle sizes by centrifugally removing particles larger than the respective aerodynamic cut;
   flowing particles smaller than the aerodynamic cut size into an optical sensor; and
   with said optical sensor, recording aerosol concentrations as a function of the aerodynamic particle sizes determined by said aerodynamic cut device.

2. The method of claim 1 wherein the flowing of the aerosol into the aerodynamic cut device includes flowing the aerosol into all aerodynamic cut device having a rotary element selected from a group consisting essentially of one or more disc or propeller blades mounted on a shaft, or an impeller with radial, forward-curved or backward-curved blades.

3. The method of claim 1 wherein the optical sensor has an inlet and the method further comprises rotating the rotary element about an axis of said rotating element that is either parallel or perpendicular to the inlet to said optical sensor.

4. The method of claim 1 further comprising increasing the rotational speed of said rotating element from zero to a high number of revolutions per minute.

5. The method of claim 4 wherein the increasing of the rotational speed of said rotating element gives aerodynamic cuts at the successively smaller aerodynamic particle sizes.

6. The method of claim 1 further comprising removing particles larger than said aerodynamic cut size to the inner wall of said aerodynamic cut device.

7. The method of claim 6 further comprising retaining removed particles with a sticky substance on said inner wall or on a removable insert attached to the surface facing said rotating element.

8. The method of claim 1 further comprising providing a flow splitter attached to an exit opening of said aerodynamic cut device so that said optical sensor samples all or a fraction of the aerosol flow exiting from said aerodynamic cut device.

9. The method of claim 1 further comprising measuring the aerosol by aerosol photometry or by optical single particle size spectrometry.

10. The method of claim 9 further comprising utilizing an aerosol photometer to record light scattering signals emitted by the aerosol particles as the particles exit from said aerodynamic cut device while said rotating element is continuously or intermittently changing its speed of rotation.

11. The method of claim 10 wherein differences in said light scattering signals from said aerosol photometer are related to the particle count, surface, volume or mass in the aerosol size range corresponding to the speed of rotation of said rotating element in said aerodynamic cut device.

12. The method of claim 9 further comprising utilizing an optical single particle counter to record the particle size distribution as a function of aerodynamic particle size by relating the aerodynamic cuts obtained through operation of said aerodynamic cut device to the optical sizes of the optical single particle counter.

13. An apparatus for determining the concentration of airborne particles in an aerosol as a function of aerodynamic particle size comprising:

a variable setting aerodynamic cut device having an inlet and an outlet and that is operative to remove from the aerosol particles larger than an aerodynamic particle cut size;

an aerosol sensor connected to the outlet of the cut device to receive from the aerodynamic cut device aerosol from which larger particles have been removed, the sensor being operative to measure concentrations of airborne particles in the aerosol received from the cut device; and a controller operative to vary the setting of the aerodynamic cut device through successively different rotational speeds. and, at each successively different speed, recording the measured concentration as a function of the aerodynamic particle size at which the aerodynamic cut is made.

14. The apparatus of claim 13 wherein:

the controller is operative to vary the setting of the aerodynamic cut device through successively increasing rotational speeds to make successive cuts at successively smaller particle sizes.

15. The apparatus of claim 14 wherein the controller is operative to vary the setting of the aerodynamic cut device from zero to a high rotational speed.

16. The apparatus of claim 13 further comprising:

a flow control device connected in series with the aerodynamic cut device to maintain the flow rate of aerosol into the cut device substantially constant.

17. The apparatus of claim 16 wherein:

the flow control device includes a pump arranged to force a flow of aerosol through the aerodynamic cut device so as to maintain a substantially constant flow rate.

18. The apparatus of claim 16 wherein:

the flow control device includes a flow restrictor operative to restrict the flow of aerosol through the aerodynamic cut device to a substantially constant flow rate.

19. The apparatus of claim 13 wherein:

the cut device includes a rotary element having at least one blade mounted on a shaft.

20. The apparatus of claim 13 wherein:

the cut device includes an inner wall coated with a sticky substance for retaining particles from the aerosol.

21. The apparatus of claim 13 further comprising:

a flow splitter connected to the outlet of the cut device and operable to control the fraction of the aerosol from the cut device to the aerosol sensor.

22. The apparatus of claim 13 wherein:

the aerosol sensor includes an optical single particle size spectrometer.

23. The apparatus of claim 13 wherein:

the aerosol sensor includes an aerosol photometer or aerosol mass sensor.

24. The apparatus of claim 13 wherein:

the aerosol sensor includes an optical single particle size spectrometer; and the controller is operative to record the particle size distribution as a function of aerodynamic particle size by relating the aerodynamic cuts obtained through operation of the aerodynamic cut device to the optical sizes of the optical single particle counter.

25. A method for determining the concentration of airborne particles as a function of aerodynamic particle size, the method comprising:

(a) inputting aerosol that includes air and airborne particles into an aerodynamic cut device while rotating a rotary element;

(b) making with the aerodynamic cut device an aerodynamic cut at an aerodynamic particle size that varies inversely with the rotational speed of the element by centrifugally separating into classes particles larger than the aerodynamic particle size at which the cut is made and particles smaller than the aerodynamic particle size at which the cut is made;

(c) flowing, from the aerodynamic cut device to an aerosol sensor. aerosol containing air and the airborne particles in one of the classes;

(d) measuring with the aerosol sensor the concentration of airborne particles in the flowing aerosol; and (e) recording the measured concentration as a function of the aerodynamic particle size at which the aerodynamic cut is made.

26. The method of claim 25 further comprising:

rotating the rotary element at a plurality of different rotational speeds and performing (a) through (e) at each rotational speed of the plurality.

27. The method of claim 26 further comprising:

the rotating of the rotary element at the plurality of different rotational speeds includes successively increasing the rotational speed of the rotary element to make successive cuts at successively smaller particle sizes.

28. The method of claim 27 wherein the rotational speed of the rotating element is continuously or intermittently increased from zero to a high rotational speed.

29. The method of claim 26 further comprising:

providing a flow control device connected in series with the dynamic cut device to maintain the flow rate of aerosol through the device substantially constant.

30. The method of claim 29 wherein:

the providing of a flow control device includes providing a pump and the inputting of the aerosol includes forcing a flow of aerosol through the aerodynamic cut device to maintain a substantially constant flow rate.

31. The method of claim 29 wherein:

the providing of a flow control device includes providing a flow restrictor and the inputting of the aerosol includes restricting the flow of aerosol through the aerodynamic cut device to a substantially constant flow rate.

32. The method of claim 25 wherein:

the making of the aerodynamic cut includes making the aerodynamic cut by centrifugally removing particles larger than the aerodynamic particle size at which the cut is made from aerosol that contains particles smaller than the aerodynamic particle size at which the cut is made; and the flowing of aerosol containing air and airborne particles includes the flowing from the aerodynamic cut device to an aerosol sensor of aerosol that contains the particles smaller than the aerodynamic particle size at which the cut is made.

33. The method of claim 32 wherein:

the measuring includes measuring with the aerosol sensor the total concentration of airborne particles in the flowing aerosol; and the method further comprises:

rotating the rotary element at a plurality of different rotational speeds and performing (a) through (e) at each rotational speed of the plurality, and calculating from the total concentrations measured at the different rotational speeds the concentration of each aerodynamic particle size at which the aerodynamic cut is made.

34. The method of claim 32 further comprising:

rotating the rotary element at a plurality of different rotational speeds and performing (a) through (e) at each rotational speed of the plurality.

35. The method of claim 34 further comprising:

the rotating of the rotary element at the plurality of different rotational speeds includes successively increasing the rotational speed of the rotary element to make successive cuts at successively smaller particle sizes.

36. The method of claim 35 wherein the rotational speed of the rotating element is continuously or intermittently increased from zero to a high rotational speed.

37. The method of claim 32 further comprising:

using a flow control device connected in series with the dynamic cut device to maintain the flow rate of aerosol through the device substantially constant.

38. A method for determining the concentration of airborne particles as a function of aerodynamic particle sizes, the method comprising:

(a) inputting aerosol that includes air and airborne particles into an aerodynamic cut device that is operative to make an aerodynamic cut, by rotating a rotary element, at a selected aerodynamic particle size;

(b) making with the aerodynamic cut device an aerodynamic cut at the selected aerodynamic particle size to separate into classes particles larger than the selected aerodynamic particle size and particles smaller than the selected aerodynamic particle size; to (c) flowing, from the aerodynamic cut device to an aerosol sensor, aerosol containing air and the airborne particles in one of the classes;

(d) measuring with the aerosol sensor the total concentration in the flowing aerosol of airborne particles in the one of the classes; and (e) changing rotational speed of the rotary element and thereby varying the aerodynamic cut in accordance with different selected aerodynamic particle sizes and repeating (a) through (d) for each varied cut; and (f) deriving and recording from the measured total concentrations a concentration of particles in the input aerosol for each selected dynamic particle size.

* * * * *

UNITED STATES PATENT AND TRADEMARK OFFICE
CERTIFICATE OF CORRECTION

PATENT NO.    : 6,408,704 B1
DATED         : June 25, 2002
INVENTOR(S)   : Klaus Willeke It is certified that error appears in the above-identified patent and that said Letters Patent is hereby corrected as shown below:

<u>Column 8,</u>
Line 52, reads "to operate 20 the" and should read -- to operate the --.

<u>Column 10,</u>
Line 42, reads "an-aerosol" and should read -- an aerosol --.

<u>Column 12,</u>
Line 63, reads "an, aerosol" and should read -- an aerosol --.

<u>Column 14,</u>
Line 17, reads "of the aerodynamic particle sizes. the" and should read -- of their aerodynamic particle sizes, the --.
Line 30, reads "into all aerodynamic" and should read -- into an aerodynamic --.

<u>Column 15,</u>
Line 24, reads "speeds. and" and should read -- speeds, and --.

<u>Column 18,</u>
Line 14, reads "size; to" and should read -- size; ... --.

Signed and Sealed this

Eighteenth Day of February, 2003

JAMES E. ROGAN
*Director of the United States Patent and Trademark Office*

UNITED STATES PATENT AND TRADEMARK OFFICE
CERTIFICATE OF CORRECTION

PATENT NO.     : 6,408,704 B1
DATED          : June 25, 2002
INVENTOR(S)    : Klaus Willeke It is certified that error appears in the above-identified patent and that said Letters Patent is hereby corrected as shown below:

Column 13,
Line 34, reads "RPM; to" and should read -- $RPM_1$ to --

Signed and Sealed this

Thirteenth Day of May, 2003

JAMES E. ROGAN
*Director of the United States Patent and Trademark Office*